United States Patent [19]

Fitzgerald et al.

[11] 3,976,074
[45] Aug. 24, 1976

[54] ABSORBENT ARTICLE
[75] Inventors: Harry G. Fitzgerald, Green Bay, Wis.; Donald Patience, Barrington, Ill.
[73] Assignee: Colgate-Palmolive Company, New York, N.Y.
[22] Filed: Aug. 8, 1975
[21] Appl. No.: 603,071

[52] U.S. Cl. .............................. 128/284; 128/287; 128/290 R; 128/290 P; 128/296
[51] Int. Cl.² .................... A61F 13/16; A41B 13/02
[58] Field of Search .............. 128/284, 287, 290 R, 128/290 P, 296

[56] References Cited
UNITED STATES PATENTS

| 3,777,758 | 12/1973 | Mesek | 128/284 |
| 3,804,092 | 4/1974 | Tunc | 128/284 |
| 3,837,343 | 9/1974 | Mesek | 128/287 |
| 3,901,238 | 8/1975 | Gellert | 128/290 R |

Primary Examiner—Aldrich F. Medbery
Attorney, Agent, or Firm—Powell L. Sprunger

[57] ABSTRACT

An absorbent article comprising, an absorbent pad having a mass of hydrophilic fibers and a matrix of a comminuted hydrophobic material dispersed in the interfiber spaces defined by the fibers throughout at least a portion of the pad.

18 Claims, 8 Drawing Figures

ABSORBENT ARTICLE

BACKGROUND OF THE INVENTION

The present invention relates to absorbent articles, and more particularly to disposable absorbent articles.

An assortment of absorbent articles of the disposable type have been proposed for use in receiving and retaining body fluids, such as disposable diapers and sanitary pads. The articles may have a fluid impervious backing sheet, a fluid pervious top or cover sheet, and an absorbent pad between the backing and top sheets to capture the body fluids which pass through the top sheet. The pads are commonly made from a fibrous cellulosic material which provides the desired absorbent characteristics to the pad.

Although such pads may perform their absorbent function adequately upon receipt of the first or initial surge or surges of fluid, such as urine, it has been found that absorbency in the pads during subsequent use of the articles may be impaired due to the nature of the materials in the pad while in a wet condition. In particular, when the wet cellulosic fibers are placed under loads the fibers are compacted, thus reducing the interfiber spaces between fibers in the wet pad and compromising the absorptive capacity of the pad. For example, when a disposable diaper is wet by an infant, the weight placed by the infant on the wet diaper pad may sufficiently compact fibers in the pad such that the total absorptive capacity of the pad is reduced.

Of course, a solution to the absorbency problem would be satisfactory if the over-all cost of the disposable article is not significantly increased, and would be particularly desirable if, in fact, the cost of the article to the consumer is decreased. As will be seen below, a solution of a problem related to the manufacture of such articles also resolves the difficulty associated with absorbency of the articles during use.

The materials normally utilized in making the absorbent articles, e.g. disposable diapers, are described as follows. The fluid impervious backing sheets are made of a thermoplastic material, such as polyethylene, the fluid pervious top sheets are commonly made of a fibrous nonwoven material having a hydrophobic binder, while the absorbent pads are made of an absorbent cellulosic material, such as wood fluff. The diapers are usually provided with tape fasteners for securing the diapers about infants. Such fasteners have a backing commonly made of a thermoplastic or paper material and an adhesive coating on one surface of the fastener backing. It will be seen that the basic components of the diaper are products of natural resources and are costly, viz., trees and oil, and are likely to be so in the future. Hydrocarbon feed stuffs from oil are utilized to make the backing sheets, and possibly the adhesive and backings of the tape fasteners, while fibers formed from appropriate wood pulp are utilized to make the absorbent pads, the top sheets, and possibly the fastener backings of the diapers.

Yet the manufacture of such articles, which have come into every day use, is attendant with waste resulting in disposal of large quantities of such valuable materials. For example, when manufacture of such articles is initiated on a machine, a substantial amount of the materials may be utilized before a satisfactory article is obtained for packaging and sale, and the initial portion of such materials produced during the setup procedure would normally be discarded as waste. Additional waste materials may be accumulated while the machine is not functioning properly, during unscheduled stops of the machine, after breakage of materials utilized in making the articles, or during changes of raw material sources supplied to the machine.

In each case, the rejected materials have been discarded or destroyed in the past as waste, resulting in loss of valuable natural resources. For example, the waste materials may be utilized for purposes of packing, resulting in minimal use of the materials relative their value. Alternatively, the materials may be burned or used as land fill, where permitted, which is wasteful and generally undesirable from an ecological point of view.

SUMMARY OF THE INVENTION

A principal feature of the present invention is the provision of an improved absorbent article and a method of making such an article in an inexpensive manner.

The article of the present invention comprises, an absorbent pad having a mass of hydrophilic fibers and a matrix of a comminuted hydrophobic material dispersed in interfiber spaces defined by the fibers throughout at least a portion of the pad.

A feature of the present invention is that the hydrophobic materials provide a greater wet resiliency to the pad.

Another feature of the invention is that the hydrophobic materials help maintain interfiber spaces between the hydrophilic fibers of the pad open under loads and during longer periods of time.

Thus, a feature of the present invention is that the hydrophobic materials in the absorbent pad enhance the absorptive capacity of the pad when wet and compressed during use.

A feature of the invention is that a portion of the hydrophilic fibers may be made from a waste absorbent article.

Yet another feature of the present invention is that the hydrophobic material may be made from a waste absorbent article.

Another feature of the present invention is that the absorbent pad may be made from waste absorbent articles, thus reducing the cost of the article to the consumer.

A feature of the invention is that the hydrophobic material in the pad may be formed from fused thermoplastic materials.

A further feature of the invention is that the fused materials enhance the effective fiber length of the pad relative shorter hydrophilic fibers.

Thus, another feature of the invention is that the fused materials provide a more cohesive pad which has a greater absorbent capacity and loft.

Still another feature of the invention is the provision of feed rolls containing a compressed web of hydrophobic and hydrophilic materials.

Another feature of the invention is that the hydrophobic materials are fused in the rolls and enhance the structural integrity of the rolls.

A feature of the present invention is the provision of an apparatus and a method for making the articles of the present invention from such feed rolls.

Another feature of the invention is the provision of an apparatus and a method for making feed rolls from a source of waste or raw materials containing bulk hydrophobic and hydrophilic materials.

Yet another feature of the present invention is the provision of an apparatus and a method for controlling the width and basis weight of such feed rolls.

Still another feature of the invention is that the bulk hydrophobic and hydrophilic materials are converted to a form as rolls which may be readily placed in storage or handled during manufacture of the articles.

Further features will become more fully apparent in the following description of the embodiments of this invention and from the appended claims.

DESCRIPTION OF THE PREFERRED EMBODIMENTS

Although for convenience the articles of the present invention will be described primarily as disposable diapers, it will be understood that the articles may be of any suitable type, such as sanitary napkins or maternity napkins. Also, in the description below, relating to manufacture of the articles of the present invention from waste materials, it will become apparent that the finished or new articles may be made from waste articles of the same type as the finished articles, from waste articles different than the finished articles, or from other suitable bulk materials.

Figure 1:
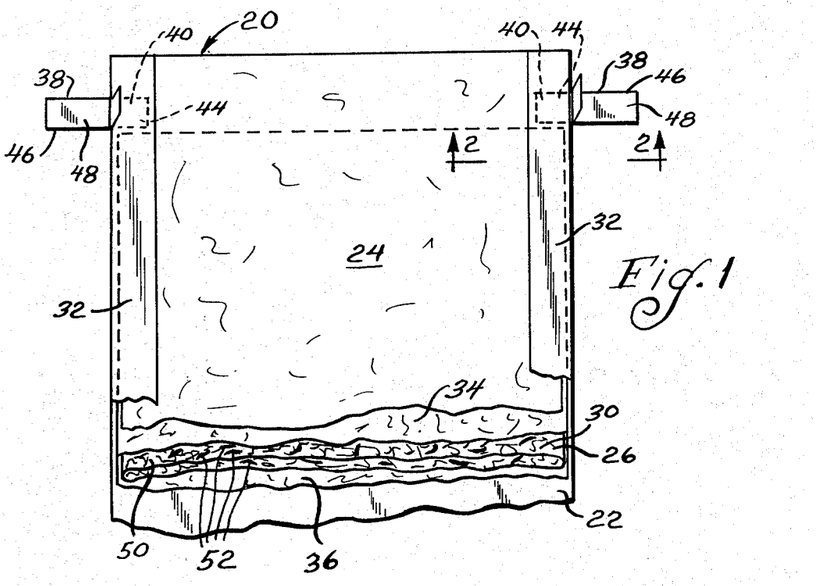
FIG. 1 is a fragmentary plan view of an absorbent article of the present invention, being illustrated in the form of a disposable diaper.
Figure 2:
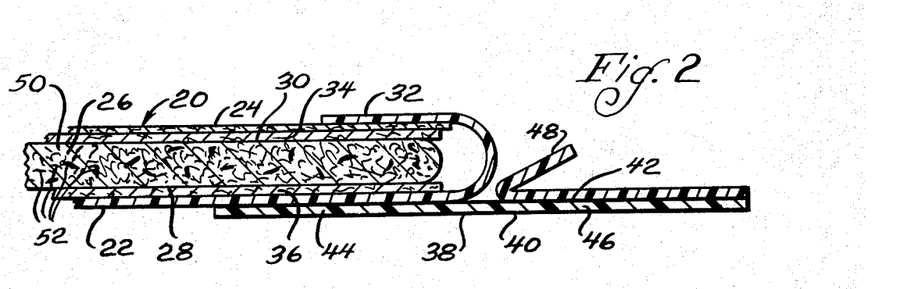
FIG. 2 is a fragmentary sectional view taken substantially as indicated along the line 2—2 of FIG. 1.

Referring now to FIGS. 1 and 2, there is shown an absorbent article or disposable diaper generally designated 20 having a fluid impervious backing sheet 22, a fluid pervious cover or top sheet 24, and an absorbent pad 26 intermediate the backing and cover sheets 22 and 24, respectively, such that the backing sheet 22 covers the back surface 28 of the absorbent pad 26, while the top sheet 24 covers at least a portion of the front surface 30 of the pad. As shown, the backing sheet 22 may have side margins 32 which are folded over and secured to the sides of the top sheet 24. The diaper may also have a top wadding sheet 34 intermediate the front surface 30 of the pad 26 and the cover sheet 24, and a back wadding sheet 36 intermediate the back surface 28 of the pad 26 and the backing sheet 22. The wadding sheets 34 and 36 serve to maintain the structural integrity and prevent balling of the absorbent pad 26 when the pad becomes wet during use.

The diaper 20 may also include a pair of conventional tape fasteners 38. The fasteners 38 may have a backing 40 with adhesive 42 coated on one surface of the backing. The adhesive 42 on one end 44 of the fasteners 38 is attached to the back surface or backing sheet 22 of the diaper, while the adhesive on the other end 46 of the fasteners may be releasably covered by a release sheet 48. During placement of the diaper, the release sheets 48 are removed from the other ends 46 of the fasteners 38, and the fasteners are utilized to secure the diaper about the infant. The diaper 20 may be utilized in its flat condition as shown, or may be folded into a box-pleat configuration, or other suitable configuration, as desired.

The materials utilized to make the diaper are described as follows. The backing sheet 22 is normally made from a thermoplastic material, such as polyethylene, while the top sheet 24 is commonly made of a nonwoven material which may include up to 20 percent by weight of a hydrophobic binder. Accordingly, the backing sheet is made of a hydrophobic material, while a reasonable proportion of the top or cover sheet 24 is made of a hydrophobic material. The remainder of the nonwoven top sheet is made of a fibrous material. The top and back wadding sheets 34 and 36, respectively, are normally made of an absorbent cellulosic fibrous material. The backings 40 of the fasteners 38 may be made of a thermoplastic material, such as polyethylene, or paper, while the adhesive 42 may have an acrylic or rubber base depending upon the particular characteristics of the adhesive desired. The release sheets 48 for the fasteners 38 may be made of suitable paper having a silicon release coating to provide a limited affinity of the sheets for the adhesive 42 on the backings 40, and permit ready removal of the release sheets from the adhesive. The absorbent pads in conventional disposable diapers or articles are frequently made from a fibrous absorbent cellulosic material.

The absorbent pads 26 of the articles or diapers 20 of the present invention have a mass of hydrophilic fibers 50 with a mixture of comminuted or fiberized hydrophobic materials 52 dispersed throughout the pad. The hydrophobic materials 52 form a matrix in interfiber spaces defined by the hydrophilic fibers 50, and, due to resiliency of the hydrophobic materials although wetted, increase the wet resiliency of the pad 26. In the absence of the hydrophobic materials, the hydrophilic fibers are compacted when wetted and placed under loads, thus closing interfiber spaces between the fibers and impairing the absorbent function of the pad. However, the hydrophobic materials dispersed in the pad of the present invention assist in maintaining the interfiber spaces of the hydrophilic fibers open when the pad is wetted and placed under loads, thus preventing collapse of the corresponding interfiber spaces in the wetted pad, and enhancing the absorbent function of the pad during extended use of the article or diaper 20.

Since conventional disposable articles include different parts which are made from various hydrophobic and hydrophilic materials, it will be seen that the use of materials of such articles are compatible with the materials required in the absorbent pads 26 of the present invention as discussed above. Thus, absorbent articles which are normally discarded as waste, resulting from the manufacture of finished articles, may be utilized in the absorbent pads of the present invention by selecting suitable quantities of the waste materials for making the pads. Accordingly, the hydrophilic materials contained in the waste articles may be formed into at least a portion of the hydrophilic fibers in the absorbent pad 26, while the hydrophobic materials in the waste articles may be reformed as the hydrophobic materials 52 in the pad 26. As previously noted, the hydrophilic materials for the pad 26 may be obtained from the waste absorbent pad, a portion of the waste top sheet, the waste top and back wadding sheets, and possibly the waste backings of the tape fasteners. The hydrophobic materials for the pad 26 may be obtained from the thermoplastic backing sheet, the hydrophobic portion of the top sheet, and possibly the backings of the tape fasteners.

It is, of course, desirable to make maximum use of the valuable materials contained in such waste articles, and, accordingly, the waste articles are preferably used, as available, in making the new pads 26, since the materials would otherwise be discarded. When not available, it is apparent that the pads 26 may be made from virgin or nonwaste hydrophilic and hydrophobic materials, as desired. It is also contemplated that waste articles which contain the pads 26 of the present invention may be utilized to make further articles, by controlling the relative proportion of the hydrophobic and hydrophilic materials in the resulting finished article. The desired structure of the absorbend pad 26 in the articles of the present invention, containing relative amounts of hydrophilic and hydrophobic materials to achieve the desired characteristics of the pad, will be described in detail below.

Figure 3A:
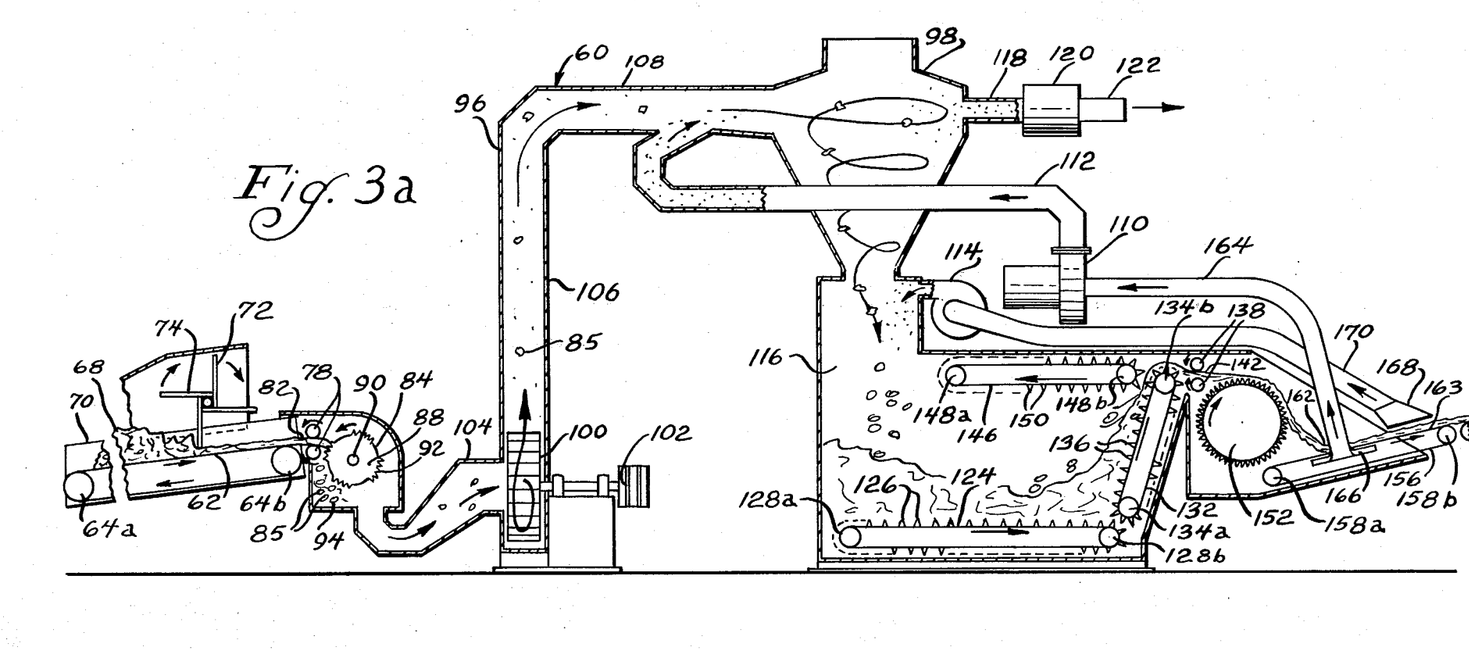
FIG. 3a and 3b are fragmentary elevational views, partly broken away, of an apparatus for making feed rolls, utilized in making the absorbent articles of the present invention, according to a method of the present invention.
Figure 4A:
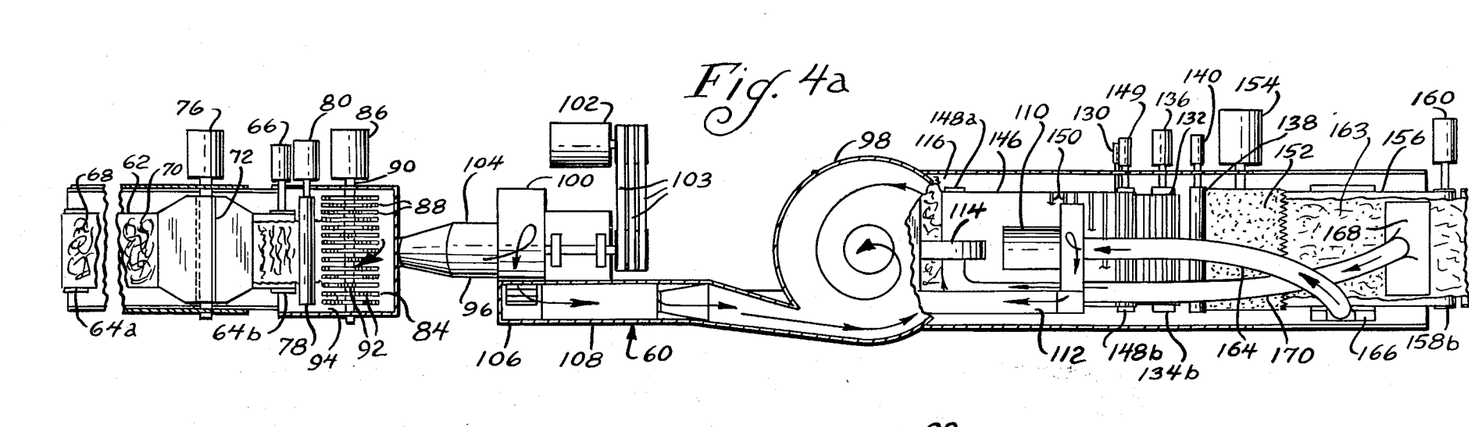
FIGS. 4a and 4b are fragmentary top plan views, partly broken away, of the apparatus of FIGS. 3a and 3b.

Turning now to FIGS. 3a and 4a, an apparatus 60 is illustrated for making feed rolls, according to a method of the present invention, which are utilized in making the absorbent pads 26 for the diapers or articles 20 of the present invention. As shown, the apparatus 60 has an endless conveyor belt 62 supported by a pair of rollers 64a and 64b, with the roller 64b and the belt 62 being driven by suitable drive means 66, such as a motor. The belt 62 has an extended length, such that sufficient space is provided for placement of bulk raw materials 68, which are utilized to make the feed rolls, on an uncovered region 70 of the belt 62. As previously indicated, the raw materials 68 may be waste materials which have been rejected from the manufacturing line, and may be delivered to the apparatus 60 from the line in extended or relatively short lengths, depending upon the condition during manufacture which causes rejection of the articles as unpackaged goods. As desired, bulk waste or virgin hydrophobic and hydrophilic materials may be placed on the conveyor belt 62 at region 70, either separately or in combination, and in relative amounts to achieve the desired proportions of hydrophobic and hydrophilic materials in the feed rolls, and ultimately in the absorbent pads.

The raw materials 68 are then moved by the belt 62 toward a paddle 72, as indicated by direction of the arrows in the drawings, having a plurality of blades 74. The paddle 72 is rotatably driven by drive means 76, such as a motor, in a clockwise direction, such that the ends of the blades 74, which are spaced slightly from the belt 62, repetitively return an excess portion of the materials 68, if any, back toward the placement region 70 of the belt 62. Accordingly, the paddle 72 and blades 74 serve to limit the quantity of bulk materials which are passed beneath the paddle 72, in order to maintain the amount of materials transported to shredding means, described below, in manageable quantities.

The materials 68 which pass beneath the blades 74 of the paddle 72 are transported by the belt to a pair of spaced rolls 78 which are driven by drive means 80, such as a motor, in opposite directions, as indicated by the direction of the arrows in the drawings. The materials 68 thus pass into the nip 82 between the rolls 78, where the materials are held while a shredder 84 tears the materials into relatively small hydrophobic and hydrophilic particles 85. The shredder 84 may be of any suitable type, such as a device having a plurality of spaced blades 88 mounted on a rotatable rod 90, with the blades 88 having projecting teeth 92 spaced around the periphery of the blades. The rod 90 and blades 88 are rotated by drive means 86 in a counterclockwise direction, such that the teeth 92 rip apart or shred the materials retained by the rolls 78, with the shredded particles collecting in a chamber 94 below the blades 88.

As will be seen below, the shredded particles will be later reduced to particles or fibers of yet a smaller size. For convenience in terminology, various terms, such as shredding, fiberizing, and comminuting, will be used interchangeably to designate a similar result, viz., breaking down and reducing the average size of materials, such as pieces, particles, or fibers, to particles or fibers of an average smaller size. This result may be accomplished by suitable apparatus which tear apart, shred, rip, pulverize, or perform similar functions. Such apparatus include shredders, hammermills, fiberizers, pin cylinders, or other devices of similar nature designated by various terms in the art.

A closed air transport system 96 is provided for moving the particles 85 from the chamber 94 to a cyclone separator 98, while preventing the particles from escaping to the atmosphere. A blower 100, driven by drive means 102 through belts 103, draws the particles from the chamber 94 through a connecting conduit 104, and blows the particles through a verticle conduit 106 and a horizontal conduit 108 into the separator 98.

As shown in the drawings, the air and particles are moved in a generally circular or spiral path inside the separator 98, such movement being induced by the air arriving in the separator from the blower 100, the air blown by a blower 110 through a conduit 112 into the horizontal conduit 108 and thence the separator 98, and the air driven into the system below the separator 98 by a blower 114. As the entrained particles of various size are driven in this circular path, the heavier particles move toward the central region of the separator 98, and eventually settle into a lower chamber 116, where the heavier particles are collected. At the same time, the residue of lighter particles, such as powder and dust, move to the outer portion of the circular trajectory, and eventually pass through a tube 118 to a filter 120, where the residue of lighter particles are collected while the filtered air passes into the atmosphere through an exhaust tube 122.

The heavier particles are thus separated and deposited in the chamber 116 adjacent one end of an endless, horizontally disposed, conveyor belt 124. The belt 124 has a plurality of spikes 126 projecting outwardly from its outer surface. The spikes 126 may be arranged in lateral rows on the belt with the rows being suitably spaced completely around the longitudinal periphery of the belt. As shown, the belt is supported by a pair of rollers 128a and 128b, with the roller 128b being driven by suitable drive means 130, such as a motor. The materials or particles which are deposited in the chamber 116 collect in a pile on top of and around the belt 124, and the belt 124 transports the overlying materials toward an endless belt 132, as indicated by the direction of the arrow in the drawings, which is preferably disposed at an acute angle relative the vertical direction. Thus, so long as particles are located on the upper reach of the belt 124, the materials are continuously supplied by the belt 124 to the belt 132. If the particles collect in a considerable pile above the belt 124, the materials adjacent the upper reach of the belt 124 are dislodged from the pile by the spikes 126, and are moved toward the belt 132. Since the belt 124 is slightly spaced from the lower end of the chamber 116, as shown, it is apparent that the spikes 126 on the lower reach of the belt serve to remove materials from below the belt for subsequent transportation to the belt 132.

The belt 132 is supported by a pair of rollers 134a and 134b, and has a plurality of spikes 136 projecting outwardly from its outer surface in a configuration similar to that described in connection with the belt 124. The belt 132 is driven by suitable drive means 136, such as a motor, in a clockwise direction, as viewed in the drawings, such that the particles supplied by the belt 124 are lifted by the spikes 136 toward the upper turn of the belt 132. Thus, movement of the belts 124 and 132 result in a supply of particles at the upper turn of belt 132, for a purpose described below. If a substantial pile of materials have collected in the chamber 116, a general shifting of the pile toward the upper turn of belt 132 will take place.

As shown in the drawings, a portion of the particles which are lifted by the belt 132 pass over the upper turn of belt 132 to the nip 142 between a pair of rolls 138. However, an endless belt 146, which is supported horizontally by a pair of rollers 148a and 148b, returns an excess portion of the particles lifted by belt 132 for subsequent conveyance. The roller 148b and belt 146 are driven by drive means 149, such as a motor, in a clockwise direction, as indicated by the direction of the arrow in the drawing. As shown, the right turn of belt 146 is spaced slightly from the belt 132 adjacent the upper turn of belt 132. Thus, a plurality of spikes 150 projecting outwardly from the belt 146, which may be arranged as described in connection with the spikes on belt 124, remove an excess quantity of materials from the belt 132, and drop the excess particles on the particle collection above the belt 124 for subsequent transport to the belt 132. At the same time, the belt 146 permits a limited quantity of particles to pass to the upper turn of belt 132. Thus, the belts 146 and 132 co-operate to limit the quantity of particles supplied to the rolls 138. It will be apparent that the quantity of materials supplied to the rolls 138 may be controlled by the relative spacing between the belts 146 and 132, and by the rotational speeds of the various belts 124, 132, and 146.

The rolls 138 are driven in opposite rotational direction, as indicated by the direction of the arrows in the drawings, by suitable drive means 140, such as a motor. Thus, the particles supplied by the belt 132 at the nip 142 of the rolls 138 are passed through the nip to a fiberizer 152, such as a pin cylinder. It will be apparent that the quantity of materials supplied by the rolls 138 to the fiberizer 152 may be controlled, in part, by the spacing between the rolls 138 and by the rotational speed of the rolls.

The fiberizer 152 is driven in a clockwise direction by suitable drive means 154, as indicated by the direction of the arrow in the drawing, and reduces the particles passing from rolls 138 into a finer size as relatively small particles, shreds and fibers, including hydrophobic and hydrophilic materials. The fiberizer 152 also deposits the comminuted particles or fibers at a location 162 on the upper reach of an endless screen 156 as a fibrous mass. The screen 156 is supported by a pair of rollers 158a and 158b, with the screen 156 and roller 158b being driven in a clockwise direction by suitable drive means 160, such as a motor, such that the fibrous mass deposited on the screen is continuously transported away from the location 162, with the fibrous mass being formed as a fibrous layer or web 163 on the upper reach of the screen 156.

The blower 110 is connected through a conduit 164 to a vacuum inlet plate 166 which is supported beneath the upper reach of screen 156 in the region of location 162, and serves as a source of vacuum supplied to the fibrous web through conduit 164, plate 166 and the screen 156. Thus, air is drawn through the screen into the plate 166 throughout a longitudinal region of the screen at location 162 due to elongation of the plate along the screen, and the vacuum source thus draws the fibrous mass passing from the fiberizer 152 against the screen. It will be apparent that the thickness of the fibrous web 163 formed on the screen 156 is partly determined by the rotational speed of the screen 156, since a greater thickness of fibers will be collected on the screen for slower speeds of the screen, while a lesser thickness of the fibers will collect at a given location on the screen responsive to relatively higher speeds of the screen. Also, the thickness of the web formed on the screen 156 may be controlled by the blower 110, with a greater source of vacuum drawing an additional amount of fibers onto the screen, resulting in a thicker web on the screen. As will be seen below, the relative thickness of the web formed on the screen 156 ultimately determines the basis weight of the feed rolls formed by the apparatus 60. Thus, the thickness of the web 163 and basis weight of the feed rolls may be controlled in various manners, as described above, by making suitable modifications to the following: (a) rotational speeds of belts 124, 132, and 146; (b) the spacing between belts 132 and 146; (c) the rotational speeds and spacing of rolls 138; (d) the rotational speed of screen 156; and (e) the vacuum source of blower 110.

An excess of fibers from the web 163 may pass into the plate 166 due to the vacuum supplied by the blower 110. Such fibers pass through the conduit 164, the blower 110, and the conduit 112 into the horizontal conduit 108 and the separator 98, where they are again separated into heavier and lighter particles, as previously described. As the fibrous web 163 on the screen 156 is transported away from the fiberizer 152 and location 162, as shown in the drawings, any excess or loose particles or fibers from the web are removed by a relatively slight vacuum source supplied by the blower 114 through a conduit 170 to a vacuum inlet member 168, which is spaced slightly from the web 163 laterally across the screen. The vacuum source is sufficiently small to prevent removal of the web 163 from the screen 156, and the loose fibers are transported by the source through the conduit 170 and blower 114 to the chamber 116 for subsequent passage to the fiberizer 152.

Figures 3B, 5:
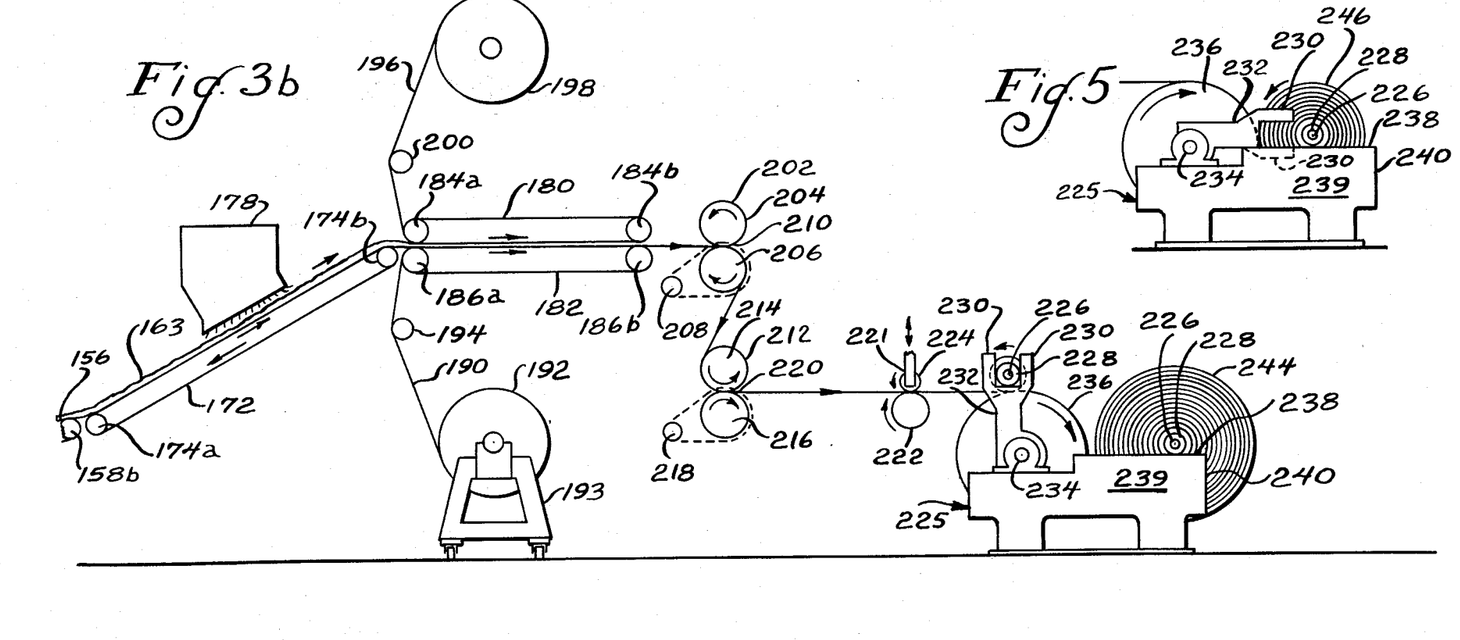
FIG. 5 is an elevational view of a portion of a roll winding apparatus which is shown in a different configuration from that illustrated in FIGS. 3b and 4b.
Figure 4B:
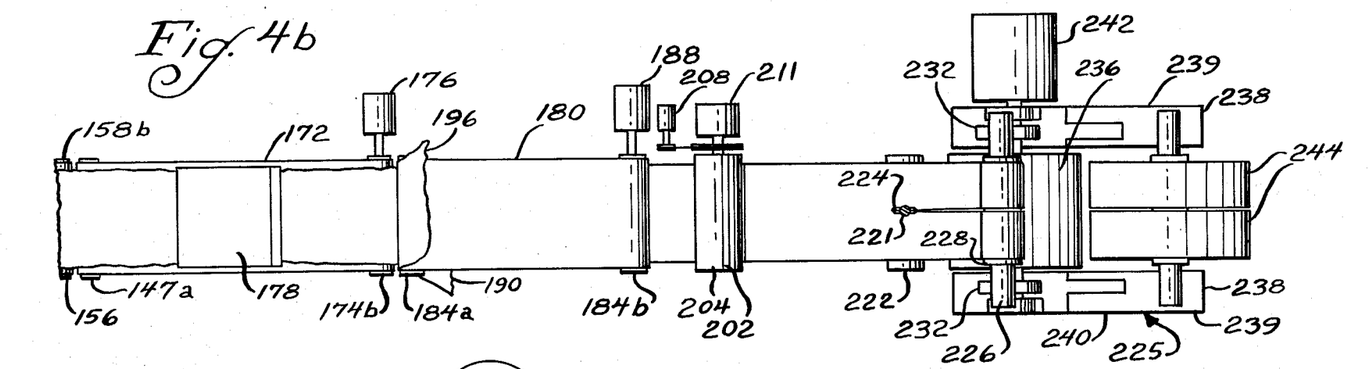

As illustrated in FIGS. 3a, 3b, 4a, and 4b, the fibrous web 163 is transported by the screen 156 onto an endless belt 172 which has a somewhat greater slope in the vertical direction. As illustrated in FIGS. 3b and 4b, the belt 172 is supported by a pair of rollers 174a and 174b, with the roller 174b and belt being driven by suitable drive means 176, such as a motor, in a clockwise direction, such that the fibrous web 163 is moved toward the upper turn of the belt 172, as indicated by the direction of the arrows in the drawings. A spraying device 178 sprays a liquid, such as water, onto the fibrous web 163 as it is moved on the belt 172, in order to wet the web and facilitate integration of its fibers during a subsequent calendering procedure, as will be described below.

The fibrous web 163 then passes between a pair of aligned and slightly spaced endless belts 180 and 182 which compress the web and reduce its loft. The belt 180 is supported by a pair of rollers 184a and 184b, while the belt 182 is supported by a pair of rollers 186a and 186b, with the rollers 184b and 186b and webs being rotatably driven in opposite directions by suitable drive means 188, such that the web is transported through the spacing between the webs 180 and 182 while being compressed.

A web 190 of tissue is unwound from a roll 192 supported on a stand 193, and passes over a roller 194 to a location intermediate the fibrous web 163 and the belt 182, such that the tissue web 190 is placed against one surface of the fibrous web 163. If desired, a second web 196 of tissue may be placed against the opposing surface of the fibrous web 163, as shown, with the web 196 being unwound from a roll 198 and being passed over a roller 200 to a location intermediate the fibrous web 163 and the belt 180. Thus, the web 163 may be placed on a single tissue 190, or may be placed between the tissues 190 and 196, as desired. In either event, the tissue web means serves as a carrier and surface structure for the fibrous web 163 after it passes from the belts 180 and 182.

As shown, the compressed or compacted fibrous web passes through the nip 210 between a pair of metal rolls 204 and 206 in a calender 202. The calender rolls 204 and 206 are driven in opposite rotational directions by suitable drive means 208, as indicated by the direction of the arrows in the drawings. The rolls 204 and 206 are also heated by a suitable means 211, such as a heat transfer system for each roll utilizing hot oil to generate the desired temperatures at the surfaces of the rolls.

Thus, the fibrous web is simultaneously heated and compressed by the calender rolls 204 and 206 as it passes through the nip 210 of the calender 202 resulting in formation of a compacted web passing from the calender. It will be recalled that compaction of the fibers in the web is facilitated by the liquid added to the web by the spraying device 178. Also, since a portion of the hydrophobic materials in the fibrous web are preferably thermoplastic, the heated rolls 204 and 206 fuse the thermoplastic hydrophobic materials in the compressed web and bind the fibers together to provide structural integrity for the compressed web in addition to that provided at the surface of the compressed web by the tissue web 190 or webs 190 and 196.

The compressed or compacted web is then passed around the outer surface of roll 206 to a second calender 212 where the web is again heated and further compressed. As shown, the calender 212 has a pair of rolls 214 and 216 which are driven in opposite rotational directions by suitable drive means 218. The rolls 214 and 216 are also heated by the heating means in a manner as described in connection with the calender 202. If desired, the calenders 202 and 212 may be operated at different temperatures, and, in a configuration found suitable, the surface temperature of the rolls 204 and 206 of calender 202 may be approximately 190° to 300°F, while the surface temperature of the rolls 214 and 216 of calender 212 may be approximately 300° to 400°F.

The compressed web then passes from the nip 220 of rolls 214 and 216 to a knife-over-roll device 221 where the web may be slit, if desired. As shown, the device 221 has a roller 222 which provides a supporting surface for the web while it is slit. The device 221 also has a rotatably mounted blade 224 which may be moved into position against the web to perform the slitting operation. The blade 224 may be selectively moved to a vertical location spaced from the web, as indicated by the arrows in the drawings, by suitable means if it is undesired to slit the web. As will be seen below, when the web is slit by device 221 a plurality of feed rolls are simultaneously formed, while a single feed roll is formed if the web is not slit. It is apparent that more than two webs may be formed, as desired, by providing a suitable number of knife-over-roll devices, or other cutting means, spaced laterally across the web.

The apparatus 225 for winding feed rolls is described as follows. The apparatus 225 has a pair of laterally spaced fork members 232 pivotally mounted on a table 240 by pivotal supports 234. The fork members 232 may be moved between an upright position while formation of a feed roll is initiated, as shown in FIGS. 3b and 4b, and a horizontal position during a later stage of the winding procedure, as shown in FIG. 5. The apparatus 225 has a plurality of mandrels 226 on which the feed rolls are wound. As illustrated in FIGS. 3b and 4b, each of the fork members 232 has a pair of tines 230 to receive the ends of the winding mandrels 226 while the fork members are in an upright position. Subsequently, the ends of the mandrels 226 are supported on a surface 238 provided by a pair of spaced arms 239 in the table 240. The apparatus also has a resilient surface winding roll 236 which is mounted for rotational movement and driven in a clockwise direction by suitable drive means 242.

The formation of feed rolls by the apparatus from the compressed web is described as follows. If the web has been slit by the device 221, a plurality of paper cores 228 corresponding to the widths of the slit webs are placed on a mandrel 226. If the web has not been slit, a single paper core may be positioned on the mandrel 226. Next the fork members 232 are placed in their upright position, as shown in FIGS. 3b and 4b, and the mandrel 226 containing the core or cores 228 is positioned in the tines 230 of the fork members, while the end of the compressed web or slit webs is wound in a counterclockwise direction around the paper core or cores one or more turns, such that the web is positioned intermediate the mandrel and the surface winding roll 236.

As shown, the openings defined by the tines 230 are sufficiently deep to permit the mandrel 226 to bear against the winding roll 236. Accordingly, the outer surface of the winding roll 236 frictionally engages the web, and surface movement of the roll 236 is imparted to the web and mandrel 226 through the core or cores 228. Since the mandrel is permitted to rotate in the tines 230, the rotational movement of the winding roll 236 in the clockwise direction results in a corresponding counterclockwise rotation of the mandrel 226 while the web is wound on the mandrel. As the web is thus surface wound onto the mandrel, the diameter of the new feed roll on the mandrel is gradually increased, such that the distance between the mandrel and the winding roll 236 is increased. However, the new feed roll continues to bear upon the outer surface of the winding roll 236, thus maintaining frictional engagement between the outer surface of the winding roll 236 and the web, resulting in initial formation of the feed roll while the mandrel 226 rises relative the winding roll 236.

Prior to the time at which the mandrel 226 is located at a position above the tines 230, a completed feed roll 244, which has the ends of its mandrel 226 resting on the support surface 238, is removed from the table 240 for storage and subsequent use. After the feed roll 244 has been removed, the fork members 232 are moved to their horizontal position, as shown in FIG. 5, such that the mandrel 226 of the new feed roll 246 rests upon the support surface 238 of the table 240. In this configuration, the tines 230 of the fork members are located in a position to permit freedom of movement and rotation of the mandrel 226 along the support surface 238.

Additionally, the new feed roll 246 continues to bear against the outer surface of the winding roll 236, such that frictional engagement between the web and the winding roll is maintained, resulting in a continued surface wind of the feed roll 246 while the feed roll and mandrel 226 rotate in a counterclockwise direction. As the diameter of the feed roll 246 increases, the axis of the mandrel is displaced toward the right of the table 240, as viewed in the drawing. After a sufficient length of the web has been surface wound onto the mandrel, the web is severed transversely across the web, the fork members 232 are again pivoted to their upright position, as previously described in connection with FIGS. 3b and 4b, another mandrel is placed in the tines, formation of a new feed roll is initiated, and the completed feed roll is removed from the table. It is apparent that if the web was slit into a plurality of webs by the device 221, a corresponding number of feed rolls are simultaneously formed on their respective paper cores.

Thus, feed rolls are made by the apparatus 60 from an initial supply of bulk hydrophilic and hydrophobic materials. The waste materials are converted into a compressed web containing the hydrophobic and hydrophilic materials, and the compressed web is wound into feed rolls for convenience in handling during storage and subsequent use for making articles of the present invention, as described below.

According to a method of the present invention, a source of waste or bulk hydrophobic and hydrophilic materials is thus shredded by a shredder into particles, while limiting the quantity of the materials supplied to the shredder. The shredded particles are transported by air from a first shredding location to a second separating location where the lighter and heavier particles are separated. The shredded particles are moved by air in a generally circular path, the lighter particles are removed from the path and are discarded, and the heavier particles are collected.

The collected heavier particles are transported to a fiberizer, where the particles are comminuted or fiberized into a fibrous web containing a mixture of hydrophobic and hydrophilic materials, while limiting the quantity of particles supplied to the fiberizer. The comminuted particles passing from the fiberizer are placed on a movable member which provides an endless supporting surface at the location of placement, while moving the member relative the location to form a layer on the member as the fibrous web.

The comminuted particles are drawn against the member with a source of vacuum, and the thickness of the fibrous web may be controlled by controlling the vacuum source to control the rate at which the particles are drawn against the member by the source. The thickness of the fibrous web may also be controlled by controlling the rate of movement of the member relative the location of placement on the member. Excess fibers may be returned from the fibrous web to the circular path or to the collection of heavier particles.

Next, the fibrous web is wetted and placed against a carrier web, after which the web is compressed to reduce its loft. The web is then simultaneously heated and compressed one or more times to produce a compressed web in which the thermoplastic hydrophobic fibers are fused. The compressed web is wound into feed rolls subsequent to a slitting procedure, if desired, to vary the width of the feed rolls formed.

Figure 6:
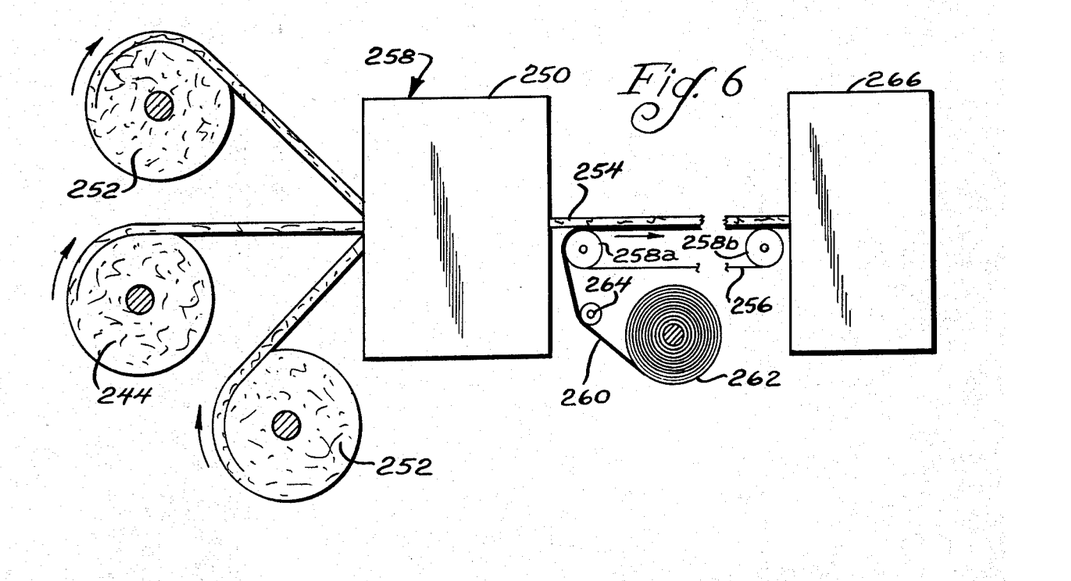
FIG. 6 is a fragmentary elevational view illustrating apparatus for making absorbent pads for the articles of the present invention from a plurality of feed rolls, according to a method of the present invention.

An apparatus 258 for utilizing the completed feed rolls 244 for making the absorbent pads of the present invention containing a mixture of hydrophilic and hydrophobic fibers will be described in connection with FIG. 6. As shown in the drawing, the completed feed roll 244 is supported for rotational movement, such that the compressed web may be unwound from the roll 244 and passed into a fiberizing or comminuting apparatus 250, such as a hammermill. One or more additional feed rolls 252 containing a compressed web of virgin hydrophilic materials may also be supported for rotational movement, in order that their webs may be unwound and passed into the apparatus 250 which simultaneously comminutes the compressed webs from the feed rolls 244 and 252. The apparatus thus reduces the webs to fibers or particles of hydrophobic and hydrophilic materials, and forms a fibrous web 254, which is passed onto an endless conveyor belt 256, supported and driven by a pair of rollers 258a and 258b. A carrier web 260, such as cellulose wadding, is unwound from a roll 262, passed over a roller 264, and placed against the fibrous web 254 at a location intermediate the web 254 and belt 256. The fibrous web 254 and carrier web 260 are then transported by the belt 256 to an apparatus 266 of known type which cuts and forms the webs into sections as absorbent pads. The pads, containing a mixture of hydrophobic and hydrophilic materials, are then made into suitable disposable articles or diapers, as desired.

Thus, the feed roll 244 may be used in conjunction with feed rolls containing solely hydrophilic materials to form a fibrous web which is cut into sections as absorbent pads for the articles of the present invention. It will be apparent that the relative proportion of the hydrophobic and hydrophilic materials contained in the pads may be determined in a number of manners. Initially, the relative amounts of the webs from the feed roll 244 and the remaining feed rolls 252 pulverized by the apparatus 250 may be controlled by the number of hydrophilic feed rolls 252 utilized simultaneously in conjunction with feed roll 244. Also, the width of the feed roll 244 relative the width of the feed rolls 252 may be controlled by the slitting device 221 described in connection with FIGS. 3b and 4b. Thus, varying widths of feed roll 24 relative a given width of the rolls 252 will result in corresponding varying proportions of the feed roll 244 and hydrophobic materials being introduced into the fibrous web 254 and absorbent pads.

Additionally, as described in connection with FIGS. 3a and 4a, the thickness of the fibrous web 163 formed on the screen 156 may be suitably modified to control the thickness and basis weight of the compressed web which is formed into the feed rolls. Thus, as shown in FIG. 6, the thickness of the compressed web from the feed roll 244 relative a given thickness of the webs in rolls 252 will also determine the relative amount of hydrophobic materials introduced into the fibrous web 254 and absorbent pads. Finally, the relative amounts of hydrophobic and hydrophilic materials introduced into the feed roll 244, and thus the pads, may be controlled by determining the relative proportions of hydrophobic and hydrophilic materials placed on the belt 62 as the source of raw material 68, as described in connection with FIGS. 3a and 4a.

Although the bulk raw materials 68 may be obtained from any suitable source, it is desirable to primarily utilize for this source those materials or articles which were previously rejected as waste from the manufacturing line. Accordingly, for convenience in discussion below the raw materials 68 will be designated as waste articles, and the various components which constitute the waste article will be preceded by the term "waste", e.g., waste backing sheet, and waste absorbent pad. The hydrophilic and hydrophobic materials contained in the web of the feed roll 244, described in connection with FIG. 6, may be termed "waste feed material", while the hydrophilic material contained in the feed rolls 252 will be called "virgin feed material". The newly formed absorbent pads containing a mixture of hydrophobic and hydrophilic materials will be designated a "new absorbent pad" or "new pad", while the completed absorbent article or diaper containing the new pad will be termed the "new absorbent article" or "new diaper", with the components of the new article being preceded by the word "new", e.g., new backing sheet.

Since the waste articles are converted to the waste feed material, the relative proportion of the waste components contained in the waste article will be similar to that contained in the waste feed material. Accordingly, the relative amounts of hydrophobic and hydrophilic materials contained in the waste feed material will be similar to the proportion of the same materials contained in the waste articles. Since the relative amounts of the waste and virgin feed materials introduced into the new absorbent pads may be determined, the proportion of hydrophobic and hydrophilic materials contained in the new pad or article may also be calculated.

As noted above, the various components of the waste article, such as the waste backing sheet or pad, may be classified generally as being a hydrophobic or hydrophilic material, or as a material containing a known proportion of hydrophobic and hydrophilic materials, such as the top sheet. Accordingly, in determining the relative amounts of hydrophobic and hydrophilic materials in the new absorbent pads, it is convenient to first calculate the relative quantities of the waste components introduced into the new pads or articles, which may be accomplished according to the following formulae:

$$W_{cn} = (W_{tcn}) \frac{(W_{cw})}{(W_{tw})}, \quad (1)$$

where, $W_{cn}$ = Weight of a particular waste component in a new article;

$W_{tcn}$ = Total weight of waste components in the new article;

$W_{cw}$ = Weight of the same component ($W_{cn}$) in the waste article; and $W_{tw}$ = Total weight of waste article.

However, since $$W_{tcn} = (W_{tpn}) \frac{(W_{tcn})}{(W_{tpn})}, \quad (2)$$

then $$W_{cn} = (W_{tpn})(P_{tcn}) \frac{(W_{cw})}{(W_{tw})}, \quad (3)$$

where, $W_{tpn}$ = Total weight of new absorbent pad; and $P_{tcn} = (W_{tcn})/(W_{tpn})$ = proportion of waste and total materials in the new pad, or proportion of waste feed materials and total feed materials introduced into the new pad.

Additionally, $$P_{cn} = \frac{(W_{cn})(100)}{(W_{tpn})}, \quad (4)$$

where $P_{cn}$ = Percentage by weight of the waste component in the new pad relative the total weight of the new pad.

As an illustration, standard size waste diapers having a total weight of 33.5 grams may be utilized to make the new absorbent pads for the articles or diapers of the present invention. The weight of the various components in each waste diaper is set forth in the following table:

TABLE I

| Component | Weight (grams) |
|---|---|
| Absorbent Pad | 21 |
| Top Sheet | 2.7 |
| Backing Sheet | 4.2 |
| Tape Fasteners | 1.1 |
| Wadding Sheets | 4.5 |

The percentage of waste feed materials relative the total amount of feed materials introduced into the new pad is selected to be 12 percent, and the weight of the new absorbent pads are also 21 grams. Accordingly, the weight of a given waste component, say the backing sheet, may be calculated from formula (3) as follows:

$$W_{cn} = \frac{(21g)(.12)(4.2g)}{(33.5g)} = .316g$$

Thus, the weight of the waste backing sheet contained in the new absorbent pad is 0.316 grams. It will be apparent that the percentage by weight of the waste backing sheet in the new absorbent pad is 1.5 percent, as determined by formula (4).

The weights and percentages of the various waste components in the new pad may be determined in a similar fashion, and are set forth in the following table:

TABLE II

| Component | Weight in Waste Article (grams) | Weight in New Pad (grams) | Percentage of Component in New Pad |
|---|---|---|---|
| Absorbent Pad | 21 | 1.580 | 7.52 |
| Top Sheet | 2.7 | .203 | .97 |
| Backing Sheet | 4.2 | .316 | 1.50 |
| Tape Fasteners | 1.1 | .083 | .40 |
| Wadding Sheets | 4.5 | .339 | 1.61 |
| Total | 33.5 | 2.521 | 12.00 |

It will be seen that the total weight of the waste components in the new pad is 2.521 grams, and that the percentage of total waste components in the new pad is 12 percent, as expected.

The relative quantities of hydrophobic and hydrophilic materials in the new pad may be readily determined as follows. Assuming that the waste tape fasteners have a polyethylene backing, the new absorbent pad will include approximately 0.083 grams of hydrophobic material, as contributed by the fasteners including adhesive. Next, it is assumed that the waste top sheet contains 20 percent by weight of a hydrophobic binder, while the remainder of the top sheet is made of a hydrophilic material. Thus, it may be determined in connection with Table II that the weight of the hydrophobic portion of the top sheet contained in the new pad is 0.041 grams. Finally, the weight of the hydrophobic backing sheet in the new pad has been determined as 0.316 grams. Accordingly, the total weight of hydrophobic materials in the new pad is the resulting sum of 0.440 grams, while the remainder of the new pad is composed of hydrophilic materials, including waste and virgin feed materials, and has a weight of 20.56 grams. Thus, the percentage by weight of the hydrophobic materials in the new pad to the total weight of the pad is approximately 2.1 percent, while the percentage by weight of hydrophilic materials in the new pad is approximately 97.9 percent. It will be apparent that the percentage by weight of the virgin hydrophilic feed materials in the new pad to the total weight of the pad is 88 percent with the weight of the virgin materials contained in each of the new pads being approximately 18.48 grams.

As previously discussed, it is desired to place a sufficient amount of the hydrophobic materials in the new pad such that the wet resiliency of the new pads or articles when placed under loads is increased, although the relative quantity of the hydrophilic materials in the new pad should not be decreased to an extent at which the total absorptive capacity of the pad is impaired. It has been found that a suitable balance between the hydrophobic and hydrophilic materials in the new pad to achieve these functions may be obtained by selecting the proportion by weight of the hydrophobic materials in the new pad to the total weight of the pad to be in the range of 1 to 15 percent, while the proportion of the hydrophilic materials by weight is in the corresponding range of 85 to 99 percent. Although the proportions of the waste components contained in a given waste article will vary somewhat depending on the structure of the article, the preferred proportions of the waste components from an average sized disposable diaper placed in the new pad of a similar diaper, as determined by the ratio of the waste component weight in the new pad to the total weight of the new pad, is set forth as follows: waste absorbent pad, 3.5 to 17.0 percent; waste top sheet, 0.5 to 2.5 percent; waste backing sheet 1.0 to 3.0 percent; waste tape fasteners 0.1 to 1.0 percent; and waste wadding sheets 1.1 to 3.2 percent. A preferred proportion by weight of the waste feed material to the total feed materials is in the range of 5.0 to 25.0 percent, while the corresponding proportion by weight of the virgin feed materials to the feed materials is in the range of 75.0 to 95.0 percent.

Thus, there has been described a new and improved absorbent article or dispaer having an absorbent pad comprising a mixture of fibrous or comminuted hydrophobic and hydrophilic materials, in order to increase the wet resiliency of the pad and article under loads and improve the absorbency of the pad during use. Particularly where the waste articles are disposable diapers, the wet resiliency of the new pads is enhanced by the relative thickness of the waste backing sheet which is normally greater than or equal to approximately 1 mil. Apparatus and methods are also provided for making feed rolls from bulk or waste raw materials, and for making the absorbent pads or articles of the present invention from the feed rolls.

Additionally, when the hydrophobic materials are formed into the new pads, these materials provide the new pads with an increased number of pad materials with longer lengths. Moreover, the thermoplastic materials, such as polyethylene, are fused into the feed rolls before these materials are comminuted into the new pads. When the fused materials are comminuted along with relatively short hydrophilic fibers in the feed roll, the effective fiber length is increased to a greater extent than such a mixture with non-fused hydrophobic materials which is believed attributable to fusing of the thermoplastic materials to the hydrophilic fibers. The longer fibers thus formed produce a pad with increased structural integrity, and greater absorbent capacity and loft.

The foregoing detailed description is given for clearness of understanding only, and no unnecessary limitations should be understood thereform, as modifications will be obvious to those skilled in the art.

We claim:

1. A disposable absorbent article for body contact to absorb body fluids comprising, an absorbent pad having a mass of hydrophilic fibers and a matrix of a comminuted hydrophobic material dispersed in interfiber spaces defined by said fibers throughout at least a portion of said pad, with at least a portion of said hydrophobic material comprising a fused comminuted thermoplastic material.

2. The article of claim 1 wherein at least a part of said thermoplastic material is fused to some of said fibers.

3. An absorbent pad of a disposable absorbent article for body contact to absorb body fluids comprising, a mixture of an absorbent fibrous cellulosic material and a hydrophobic particulate material defining together a fibrous mass for said pad, with the percentage by weight of said hydrophobic material to the total weight of the pad being in the range of 1 to 15.

4. The pad of claim 3 wherein said cellulosic and hydrophobic materials are comminuted to form said fibrous mass.

5. The pad of claim 3 wherein said cellulosic material comprises comminuted wood pulp.

6. A disposable absorbent article for body contact to absorb body fluids comprising, an absorbent pad having a fibrous mass at least partially formed from a comminuted waste absorbent article which includes as a part thereof a hydrophobic backing sheet having a thickness of greater than or equal to 1 mil.

7. A disposable article for body contact to absorb body fluids having, an absorbent pad comprising a mass of hydrophilic fibers and a comminuted waste absorbent article which includes a hydrophobic material, said comminuted waste article being mixed with said fibers to form said pad, with the percentage by weight of the waste article in the pad to the weight of the pad being in the range of 5 to 25.

8. The article of claim 7 wherein said waste article comprises a disposable diaper.

9. The article of claim 7 wherein the disposable article comprises a disposable diaper.

10. The article of claim 7 wherein said waste article includes a backing sheet of hydrophobic material, with the percentage by weight of the waste backing sheet to said pad being in the range of 1 to 3.

11. The absorbent article of claim 7 wherein said waste article includes at least one tape fastener.

12. The article of claim 11 wherein at least a portion of said fastener is made from a hydrophobic material.

13. The article of claim 11 wherein the percentage by weight of the waste fastener to said pad is in the range of 0.1 to 1.0.

14. The article of claim 7 wherein said waste article includes a top sheet of fibrous material.

15. The article of claim 14 wherein the waste top sheet includes a hydrophobic binder.

16. The article of claim 14 wherein the percentage by weight of the waste top sheet to said pad is in the range of 0.5 to 2.5.

17. The article of claim 7 wherein the percentage by weight of the waste hydrophobic material to said pad is in the range of 1 to 15.

18. The article of claim 7 in which said waste article includes a hydrophilic material, and the percentage by weight of the hydrophilic materials in said pad to the weight of said pad is in the range of 85 to 99.

* * * * *

UNITED STATES PATENT AND TRADEMARK OFFICE
CERTIFICATE OF CORRECTION

PATENT NO. : 3,976,074
DATED : August 24, 1976
INVENTOR(S) : Harry G. Fitzgerald and Donald Patience It is certified that error appears in the above-identified patent and that said Letters Patent are hereby corrected as shown below:

In column 12, line 63, "24" should be -- 244 -- .

In column 16, line 9 "dispaer" should be -- diaper -- .

Signed and Sealed this

Seventh Day of December 1976

[SEAL]

Attest:

RUTH C. MASON
*Attesting Officer*

C. MARSHALL DANN
*Commissioner of Patents and Trademarks*